United States Patent [19]

Ferchland et al.

[11] 4,401,603
[45] Aug. 30, 1983

[54] PROCESS FOR THE PREPARATION OF ARYL ISOCYANIDE-DICHLORIDES

[75] Inventors: Dieter Ferchland, Kelkheim; Ulrich Kussmaul, Niederdorfelden; Manfred Langer, Frankfurt am Main; Rolf Müller, Karben, all of Fed. Rep. of Germany

[73] Assignee: Cassella Aktiengesellschaft, Frankfurt, Fed. Rep. of Germany

[21] Appl. No.: 394,253

[22] Filed: Jul. 1, 1982

[30] Foreign Application Priority Data

Aug. 28, 1981 [DE] Fed. Rep. of Germany ....... 3134134

[51] Int. Cl.$^3$ ............................................ C07C 119/00
[52] U.S. Cl. .................................. 260/543.2; 564/218
[58] Field of Search ...................... 260/543.2; 564/218

[56] References Cited

PUBLICATIONS

Kuhle et al., Angew Chem., vol. 79, pp. 666–667, (1967).
Bly et al., J. Am. Chem. Soc., vol. 44, p. 2896, (1922).
Pettit et al., J. Org. Chem., vol. 26, p. 2563, (1961).

*Primary Examiner*—Dolph H. Torrence
*Attorney, Agent, or Firm*—Connolly and Hutz

[57] ABSTRACT

An improved process for preparation of arylisocyanide dichloride by chlorinating N-arylformamide in the presence of thionyl chloride wherein the improvement comprises preparing the N-arylformamide by formylation of an arylamine having 6 to 12 aryl carbon atoms with a formylating agent in an inert solvent.

removing excess formylating agent and by-products of the formylation thereby leaving the N-arylformamide in the form of a solution or suspension in the inert solvent and chlorinating the N-arylformamide in solution or suspension with a chlorinating agent in the presence of thionyl chloride.

11 Claims, No Drawings

PROCESS FOR THE PREPARATION OF ARYL ISOCYANIDE-DICHLORIDES

The processes for the preparation of aryl isocyanidedichlorides have been described in summary form, for example, in Angew. Chem. 79 (1967), pages 663–680. Processes suitable for the industrial preparation of aryl isocyanide-dichlorides are essentially the chlorination of isothiocyanates, the addition of chlorine to isonitriles and the chlorination of N-arylformamides in the presence of thionyl chloride.

When aryl isothiocyanates ("mustard oils") are chlorinated, sulphur dichloride is formed as an undesirable by-product as well as the desired aryl isocyanide-dichloride. In the addition reaction of chlorine with aryl isocyanates, it is necessary to process the toxic, evil-smelling and unstable aryl isocyanides. The chlorination of formanilide in the presence of chloroform and thionyl chloride (compare J. Am. Chem. Soc. 44 (1922), 2896 et seq.) gives a mixture of products and only poor yields of phenyl isocyanide-dichloride. If organic solvents are dispensed with deliberately, good yields are obtained, as a rule, in the chlorination of N-arylformamides in excess thionyl chloride (compare German Pat. No. 1,094,737). However, this known process requires the use of N-arylformamides which have been isolated and which, accordingly, must first be prepared in separate processes, isolated and dried. An additional technical effort is required for the transport and metering of the N-arylformamides, which are solid at room temperature.

It has now been found, surprisingly, that the separate preparation and isolation of the N-arylformamides is not necessary; on the contrary, the latter can be prepared by formylating arylamines in a suitable solvent and can, without being isolated, then be reacted with thionyl chloride and a chlorinating agent to give the aryl isocyanide-dichlorides. Yields of aryl isocyanide-dichlorides which are equal to, or even surpass, the best yields achievable in the state of the art are achieved in this way, at a high level of purity. This could not have been expected on the basis of the previous state of knowledge, particularly on the basis of the prejudice against the use of organic solvents in the chlorination of arylformamides.

In accordance with the process according to the invention, an arylamine having 6 to 12 C atoms, which is optionally monosubstituted or polysubstituted in the nucleus, preferably an aniline which is monosubstituted, disubstituted or trisubstituted in the nucleus, is first formylated in a manner which is in itself known in a suitable inert solvent, and is converted into the corresponding N-arylformamide. The formylation can be carried out using any agent which is capable of formylating an aromatic amino group, such as, for example, formic acid, formic/acetic anhydride, an ester of formic acid, in particular methyl formate (compare Ullmanns Encyklopädie der techn. Chemie ("Ullmann's Encyclopaedia of Industrial Chemistry"), 4th edition, volume 11 (1976), 708), or formamides, such as formamide itself or dimethylformamide (compare J. Or. Chem. 26 (1961), 2563 et seq.). Formylation using formic acid is preferred within the scope of the present invention.

The formylation is carried out in a suitable solvent or mixture of solvents. The solvent used should be inert towards the starting materials, intermediate products and end products in all the reaction stages of the process according to the invention, that is to say both in the formylation of the arylamine and in the subsequent chlorination of the N-arylformamide. Toluene, which is often used as a solvent for formylations, is not very suitable as a solvent in the process according to the invention, since it can react with the chlorinating agent. The solvent used should have a boiling point which is sufficiently different from the boiling points of the aryl isocyanide-dichloride and of thionyl chloride, in order to make it possible to separate the solvent from these compounds by distillation. Preferred solvents are those having boiling points which differ by at least 30° C. from the boiling points of the aryl isocyanide-dichloride and of thionyl chloride as is, for example, normally the case with higher alicyclic and cyclic alkanes having at least 8 C atoms in the molecule. Examples of suitable representatives are n-octane, n-nonane, n-decane, n-dodecane, n-pentadecane, 2,2,3-trimethylpentane, 2,2,3-trimethylhexane and 1,1-dimethylcyclohexane. These alkanes may also be employed in the form of their technical mixtures. In alkanes with more than 20 C atoms the melting point becomes, as a rule, too high. Polar solvents are also preferred, in particular those which have a polarity equal to or greater than that of chlorobenzene, that is to say their dipole moment is equal to or greater than that of chlorobenzene. Solvents which are very particularly preferred are those which have several or, in particular, all of the preferred properties previously mentioned, such as halogenated alicyclic alkanes having at least 2 C atoms and having, as a rule, 2 to 10 C atoms, or halogenated cycloalkanes having 5 to 10 C atoms. Higher halogenated alkanes, i.e. alkanes having at least 2 halogen atoms in the molecules, are particularly preferred, as well as monochlorinated and polychlorinated and/or mononitrated and polynitrated benzenes. The halogen atoms of the halogenated alkanes and benzenes are preferably chlorine atoms. Examples of suitable halogenated alkanes are the various chloropentanes, 1-chlorohexane and chlorocyclohexane. Examples of suitable higher halogenated alkanes are: 1,1,2-trichloroethane, 1,2,3-trichloropropane, 1,1,2,2-tetrachloroethane, 1,1,2,2-tetrachloropropane, hexachloroethane, pentachloroethane and the different tetrachloropentanes. Examples of monohalogenated and polyhalogenated and/or mononitrated and polynitrated benzenes are chlorobenzene, bromobenzene, o-dichlorobenzene, m-dichlorobenzene, p-dichlorobenzene, isomeric trichlorobenzenes, benzotrichloride, 2-chlorobenzotrifluoride, 3-chlorobenzotrifluoride, 4-chlorobenzotrifluoride, nitrobenzene, 2-chloronitrobenzene, 3-chloronitrobenzene and 4-chloronitrobenzene. Chlorobenzene, o-dichlorobenzene and nitrobenzene are preferred particularly.

In order to achieve complete conversion in the formylation, the formylating agent, preferably formic acid, is employed in a molar excess. Normally, and depending on the concentration of the formic acid employed, this excess is 1.1 times to 8 times, preferably 1.5 times to 4 times, the quantity theoretically required. The formylation is normally carried out at elevated temperature, preferably at the reflux temperature of the solvent used, and under atmospheric pressure, elevated pressure or reduced pressure. During, or subsequent to, the reaction, excess formylating agent and the by-product formed in the formylation (water in the case of formylation with formic acid and methanol in the case of formylation with methyl formate) are removed by distillation.

In many cases, such as, for example, if chlorobenzene or o-dichlorobenzene is used as the solvent, it is thereby possible to achieve virtually quantitative conversion into the N-arylformamides by azeotropic distillation of the water of reaction or excess formic acid which may be present. The N-arylformamides are produced as a solution or suspension in the solvent used.

The following are examples of arylamines which are suitable for the formylation: aniline; anilines which are monosubstituted, disubstituted or trisubstituted in the nucleus, the following being examples of possible substituents: halogen, such as, for example, fluorine, chlorine or bromine, nitro, trifluoromethyl, alkyl having, for example, 1 to 4, preferably 1 or 2, C atoms, for example n-propyl, isopropyl, n-butyl, isobutyl or tert.-butyl, preferably methyl or ethyl, alkoxy having, for example, 1 to 4, preferably 1 or 2, C atoms, such as, for example, n-butoxy or isopropoxy, preferably methoxy or ethoxy; phenyl; halogenophenyl, such as, for example, 4-chlorophenyl; phenylazo; phenoxy; halogenophenoxy, such as, for example, 4-chlorophenoxy; benzoyl; halogenobenzoyl, such as, for example, 4-chlorobenzoyl; phenylsulphonyl; halogenophenylsulphonyl, such as, for example, 4-chlorophenylsulfonyl; alkoxycarbonyl having, for example, 2 to 5 C atoms, such as, for example, methoxycarbonyl; and halogenocarbonyl, such as, for example, chlorocarbonyl. Suitable arylamines are also naphthylamines, such as, for example, 1-naphthylamine, and naphthylamines which are substituted in the nucleus. The following compounds should be mentioned as examples of starting arylamines: aniline; monohalogenoanilines, such as, for example, 2-, 3- or 4-chloro-aniline, 2-, 3- or 4-bromo-aniline, or 2-, 3- or 4-fluoro-aniline; mononitroanilines, such as, for example, 3-nitroaniline or 4-nitroaniline, dihalogenoanilines, such as, for example, 2,3-, 2,4-, 2,5-, 2,6-, 3,4- or 3,5-dichloroaniline or 2,3-, 2,4-, 2,5-, 2,6-, 3,4- or 3,5-dibromo-aniline; halogenonitroanilines, such as, for example, 2-chloro-4-nitroaniline or 4-chloro-3-nitroaniline; dihalogenonitroanilines, such as, for example, 2,5-dichloro-4-nitroaniline; halogenoalkylanilines, such as, for example, 2-methyl-4-chloroaniline or 2-chloro-6-methylaniline; dihalogenoalkylanilines, such as, for example, 2,4-dichloro-5-methylaniline, 2,4-dichloro-5-ethylaniline or 2,5-dichloro-4-ethylaniline; alkoxyhalogenoanilines, such as, for example, 2-ethoxy-4-chloroaniline; alkylnitroanilines, such as, for example, 2-methyl-5-nitroaniline, 4-methyl-3-nitroaniline or 4-ethyl-3-nitroaniline; trihalogenoanilines, such as, for example, 2,4,5-trihalogenoaniline; trifluoromethylanilines, such as, for example, 4-trifluoromethylaniline; halogenotrifluoromethylanilines, such as, for example, 2-chloro-5-trifluoromethylaniline or 2-trifluoromethyl-4-chloroaniline; alkylanilines; dialkylanilines, such as, for example, 2,4-dimethylaniline, 2,4-diethylaniline, 2,6-diethylaniline or 2,6-diisopropylaniline; trialkylanilines, such as, for example, 2,4,6-trimethylaniline, 2,4,6-triethylaniline or 2,6-diethyl-4-methylaniline; alkoxycarbonylanilines, such as, for example, 4-methoxycarbonylaniline or 4-ethoxycarbonylaniline; 4-chlorocarbonylaniline; 4-aminoazobenzene; 4,4'-dichloro-2-aminodiphenyl ether; 4-aminobenzophenone; 4-aminodiphenyl sulphone; 4-phenylaniline; and 1-naphthylamine. The yields of aryl isocyanide-dichlorides are high in cases where chlorination in the nucleus is not possible and where the nucleus does not carry one or more substituents which greatly facilitate nucleophilic aromatic substitution.

The N-arylformamides present in the solvent as a solution or dispersion are then chlorinated, in the form of the solution or suspension, advantageously in the vessel in which they were prepared, by means of a chlorinating agent in the presence of thionyl chloride. Examples of suitable chlorinating agents are elementary chlorine or chlorine donors, in particular sulphuryl chloride, because of the ease with which it can be metered. At least 1 mol of chlorinating agent and 1 mol of thionyl chloride are employed per mol of N-arylformamide. Normally, 1 to 2.5 mols of chlorinating agent are employed per mol of N-arylformamide. The use of an even higher molar excess of chlorinating agent is admittedly possible, but does not bring any advantages. Particularly good yields (up to 90%) and high degrees of purity (up to 98% or higher) are obtained if the molar ratio of thionyl chloride to chlorinating agent is greater than 1:1 and is, for example, (4 to 10):1. Even higher molar ratios of thionyl chloride to chlorinating agent are possible, but do not bring any advantages. According to the above figures, the molar ratio N-arylformamide (or arylamine, since complete formylation can be expected): chlorinating agent: thionyl chloride is normally 1: (1 to 2.5): (1 to 25), preferably 1: (1 to 2.5): (4 to 25).

It is particularly convenient to carry out the chlorination of the resulting solution or suspension of the N-arylformamide in the vessel in which this solution or suspension has been obtained. The process according to the invention thus permits the preparation of the aryl isocyanide-dichlorides to be carried out in a single vessel, starting from arylamines ("a one-pot process"). In this one-pot process, it is then possible to add the total quantity of thionyl chloride and halogenating agent employed, all at once and in a direct manner, at the temperature necessary for the formation of the isocyanide-dichloride. Surprisingly, this procedure does not amount to a safety risk, since the intermediary products, which are initially insoluble, only dissolve gradually as the reaction proceeds, and the heat of the reaction is removed, without external cooling, by means of the reaction gases which are evolved. It is, of course, also possible, however, to meter in thionyl chloride and/or halogenating agent in the course of the reaction. It is also possible initially to take a mixture of thionyl chloride and halogenating agent and to meter in the solution or suspension of the N-arylformamide, which also leads to good, and in some cases even slightly improved, yields of aryl isocyanide-dichlorides.

The chlorination is carried out at temperatures of 0° C. to 80° C.; particularly advantageous results are achieved at temperatures of 10° to 60° C.

After the completion of the chlorination, simple distillation, preferably under reduced pressure, makes it possible to regenerate excess thionyl chloride and, in some cases, chlorinating agent and also the organic solvent, and to isolate the aryl isocyanide-dichlorides.

EXAMPLE 1

162 g (1 mol) of 2,4-dichloroaniline are dissolved in 220 ml of o-dichlorobenzene and are converted quantitatively into N-2,4-dichlorophenylformamide by boiling with 135 ml (3 mols) of 85% strength by weight formic acid, the water of reaction and excess formic acid being removed by azeotropic distillation for 4 hours under atmospheric pressure and then for 4 hours under a pressure of 160 mbar. 86 ml (1 ml) of sulphuryl chloride and 585 ml (8.1 mols) of thionyl chloride are added all at once to the suspension at 22° C. A pronounced evolution of hydrogen chloride and sulphur dioxide begins after approx. 1 hour; these are absorbed in a 2-stage absorption process in water or sodium hydroxide solution. The maximum gas evolution (180 bubbles/minute) is observed within a period of 2 to 8 hours after adding the sulphuryl chloride and the thionyl chloride. The temperature remains at 20° to 24° C. without external cooling. The mixture is then warmed slowly to reflux temperature and excess thionyl chloride and o-dichlorobenzene (under a waterpump vacuum) are distilled off. 217.9 g of 2,4-dichlorophenyl isocyanide-dichloride are obtained by distillation.

Boiling point 124° to 128° C./18 mbar, purity by gas chromatography >98%, corresponding to a yield of 89.7%, relative to 2,4-dichloroaniline.

EXAMPLE 2

The suspension of N-(2,4-dichlorophenyl)-formamide prepared in Example 1 is metered into a mixture of 85 ml of sulphuryl chloride and 585 ml of thionyl chloride at 40° C. and in the course of 6 hours, a continuous evolution of gas (approx. 160 bubbles/minute) being observed, as in Example 1. Working up analogously to Example 1 gives: 218.8 g of 2,4-dichlorophenyl isocyanidedichloride, purity by gas chromatography >98%, corresponding to a 90.1% yield, relative to 2,4-dichloroaniline.

EXAMPLE 3

127.6 g (1 mol) of 2-chloroaniline in 250 ml of chlorobenzene are reacted in a one-pot process as in Example 1. This gives: 183.5 g of 2-chlorophenyl isocyanide-dichloride, boiling point 104°-106° C./13.3 mbar, purity by gas chromatography >98%, corresponding to a yield of 88%, relative to 2-chloroaniline.

EXAMPLE 4

The suspension of N-(2,4-dichlorophenyl)-formamide prepared in Example 1 is processed further analogously to Example 2, but, instead of sulphuryl chloride, a continuous stream of chlorine gas is passed in, so that a total of at least 1.1 mols of chlorine are added. This gives: 207.5 g of 2,4-dichlorophenyl isocyanide-dichloride, purity >98%, corresponding to a yield of 85.4%.

EXAMPLE 5

740.1 g (10 mols) of ethyl formate are added to 93.1 g (1 mol) of aniline in 200 ml of chlorobenzene, and the mixture is heated at 110° C. for 3 hours in an autoclave. Ethanol and excess ethyl formate are then removed by distillation. 1.0 mol of sulphuryl chloride and 8.1 mols of thionyl chloride are then added to the residue at 10° C., analogously to Example 1. After removing excess thionyl chloride and the chlorobenzene by distillation, 83.5 g of phenyl isocyanide-dichloride are obtained, boiling point 95° to 98° C./18 mbar, corresponding to a yield of 48.0%, relative to aniline.

The isocyanide-dichlorides indicated below can be prepared by the one-pot process in the solvents indicated, analogously to Examples 1–5.

| Example | Isocyanide-dichloride | Solvent | Yield |
| --- | --- | --- | --- |
| 6 | 4-chlorophenyl | 1,1,2,2-tetrachloroethane | 86% |
| 7 | 4-nitrophenyl | nitrobenzene | 89% |
| 8 | 2,4,5-trichlorophenyl | o-dichlorobenzene | 90% |
| 9 | 2-chloro-6-methylphenyl | chlorobenzene | 93% |
| 10 | 2-chloro-5-trifluoromethylphenyl | chlorobenzene | 75% |
| 11 | 4-methoxycarbonyl-phenyl | o-dichlorobenzene | 90% |
| 12 | benzophenone-4-isocyanide-dichloride | o-dichlorobenzene | 75% |
| 13 | 4-bromophenyl | chlorobenzene | 74% |

85 to 100% strength formic acid or formic/acetic anhydride can be used as the formylating agent in Examples 6 to 12, and methyl formate can also be used in Examples 6, 9 and 13.

What is claimed is:

1. In the process for preparation of aryl isocyanide-dichloride having 6 to 12 aryl carbon atoms by chlorinating N-arylformamide having 6 to 12 aryl carbon atoms in the presence of thionyl chloride, the improvement comprises preparing the N-arylformamide by formylation of an arylamine having 6 to 12 aryl carbon atoms with a formylating agent in an inert solvent, removing excess formylating agent and by-products of the formylation thereby leaving the N-arylformamide in the form of a solution or suspension in the inert solvent and chlorinating the N-arylformamide in solution or suspension with a chlorinating agent in the presence of thionyl chloride.

2. The process according to claim 1 wherein the arylamine is aniline or substituted aniline having up to three substituents.

3. The process according to claim 1 wherein the arylamine is naphthylamine.

4. The process according to claim 1 or claim 2 wherein formic acid is the formylating agent.

5. The process according to claim 1 or claim 2 wherein the inert solvent is a polar solvent having a dipole moment at least as large as the dipole moment of chlorobenzene.

6. The process according to claim 5 wherein the inert solvent is a halogenated alkane, halogenated benzene, nitrobenzene or a mixture thereof.

7. The process according to claim 1 or claim 2 wherein the chlorinating agent is chlorine or sulphuryl chloride.

8. The process according to claim 1 or claim 2 wherein the molar ratio of arylamine: chlorinating agent: thionyl chloride is 1: (1 to 2.5): (1 to 25).

9. The process according to claim 1 or claim 2 wherein the chlorination temperature is about 0° C. to 80° C.

10. The process according to claim 8 wherein the arylamine is 2,4-dichloroaniline.

11. The process according to claim 1 or claim 2 wherein the entire process is carried out as a one-pot process with each step being conducted in the same reaction vessel.

* * * * *